US 8,328,749 B2
Dec. 11, 2012

(12) United States Patent
Murakami et al.

(54) BLOOD PURIFICATION APPARATUS AND METHOD FOR CALCULATING A RECIRCULATION RATE FOR THE BLOOD PURIFICATION APPARATUS

(75) Inventors: Tomoya Murakami, Makinohara (JP); Masahiro Toyoda, Makinohara (JP); Yoshihiro Mori, Makinohara (JP)

(73) Assignee: Nikkiso Co., Ltd., Tokyo (JP)

( * ) Notice: Subject to any disclaimer, the term of this patent is extended or adjusted under 35 U.S.C. 154(b) by 884 days.

(21) Appl. No.: 11/548,499

(22) Filed: Oct. 11, 2006

(65) Prior Publication Data
US 2007/0083145 A1 Apr. 12, 2007

(30) Foreign Application Priority Data
Oct. 12, 2005 (JP) ................. 2005-297442

(51) Int. Cl.
*A61M 37/00* (2006.01)
*A61M 1/00* (2006.01)
*B01D 61/00* (2006.01)
*B01D 63/00* (2006.01)
*C02F 1/44* (2006.01)

(52) U.S. Cl. ............ 604/5.01; 604/4.01; 604/6.06; 604/6.11; 604/6.13; 604/6.16; 422/44; 210/96.2; 210/321.6

(58) Field of Classification Search ............. 604/4.01, 604/6.16; 422/44
See application file for complete search history.

(56) References Cited

U.S. PATENT DOCUMENTS

| | | | | |
|---|---|---|---|---|
| 4,231,366 A | * | 11/1980 | Schael | 604/6.05 |
| 4,334,988 A | * | 6/1982 | Milligan | 210/87 |
| 5,092,836 A | * | 3/1992 | Polaschegg | 604/6.11 |
| 5,312,550 A | * | 5/1994 | Hester | 210/646 |
| 5,588,959 A | * | 12/1996 | Ahmad et al. | 604/6.13 |
| 5,685,989 A | * | 11/1997 | Krivitski et al. | 210/646 |
| 5,830,365 A | * | 11/1998 | Schneditz | 210/739 |
| 5,866,015 A | * | 2/1999 | Kramer | 210/739 |
| 5,928,180 A | * | 7/1999 | Krivitski et al. | 604/6.09 |

(Continued)

FOREIGN PATENT DOCUMENTS
JP 9-173444 A 7/1997

(Continued)

OTHER PUBLICATIONS
Patent Abstracts of Japan for JP9-173444 published Jul. 8, 1997.

*Primary Examiner* — Justine Yu
*Assistant Examiner* — Adam Marcetich
(74) *Attorney, Agent, or Firm* — McDermott Will & Emery LLP (57) ABSTRACT

A blood purification apparatus includes a blood circuit having arterial and venous blood circuits, a blood pump, a blood purifying device, an indicator applying device that applies a predetermined indicator to the blood flowing extracorporeally through the blood circuit, a detecting device that detects the indicator applied by the indicator applying device, an arithmetic device that calculates, based on the indicator detected by the detecting device, a recirculation rate, and a calculating device that calculates an ideal extracorporeally circulating blood flow that results in the recirculation rate being no more than a predetermined value when the recirculation rate calculated by the arithmetic device is greater than the predetermined value. The recirculation rate is a proportion of a recirculated blood flow, which is reintroduced to the patient from the venous blood circuit and directed again to the arterial blood circuit, relative to an extracorporeally circulating blood flow.

11 Claims, 3 Drawing Sheets

U.S. PATENT DOCUMENTS

| | | | |
|---|---|---|---|
| 6,117,099 A * | 9/2000 | Steuer et al. | 604/4.01 |
| 6,153,109 A * | 11/2000 | Krivitski | 210/739 |
| 6,210,591 B1 * | 4/2001 | Krivitski | 210/739 |
| 6,537,240 B2 * | 3/2003 | Cavicchioli et al. | 604/5.01 |
| 6,548,017 B2 * | 4/2003 | Krivitski et al. | 422/44 |
| 6,582,656 B1 * | 6/2003 | Steuer et al. | 422/44 |
| 6,648,845 B1 * | 11/2003 | Gotch et al. | 604/5.01 |
| 2002/0009385 A1 * | 1/2002 | Krivitski et al. | 422/44 |
| 2002/0062098 A1 * | 5/2002 | Cavicchioli et al. | 604/5.01 |
| 2002/0128545 A1 * | 9/2002 | Steuer et al. | 600/345 |
| 2004/0067594 A1 * | 4/2004 | Mori et al. | 436/70 |
| 2004/0073153 A1 * | 4/2004 | Bosetto et al. | 604/5.03 |
| 2004/0129616 A1 * | 7/2004 | Mori et al. | 210/85 |
| 2005/0096578 A1 * | 5/2005 | Kleinekofort | 604/4.01 |
| 2006/0043007 A1 | 3/2006 | Tarumi et al. | |
| 2006/0064025 A1 * | 3/2006 | Kraemer | 600/504 |
| 2006/0254982 A1 * | 11/2006 | Kopperschmidt | 210/646 |
| 2009/0054822 A1 * | 2/2009 | Murakami et al. | 604/6.1 |

FOREIGN PATENT DOCUMENTS

| | | |
|---|---|---|
| JP | 2000-502940 A | 3/2000 |
| JP | 2001-502590 A | 2/2001 |
| WO | WO-98/32477 A1 | 7/1998 |
| WO | WO-02/053212 A1 | 7/2002 |

* cited by examiner

FIG. 6

BLOOD PURIFICATION APPARATUS AND METHOD FOR CALCULATING A RECIRCULATION RATE FOR THE BLOOD PURIFICATION APPARATUS

INCORPORATION BY REFERENCE

The present application claims priority under 35 U.S.C. §119 to Japanese Patent Application No. 2005-297442 filed on Oct. 12, 2005. The content of the application is incorporated herein by reference in its entirety.

FIELD OF THE INVENTION

The present invention relates to a blood purification apparatus and method for calculating a recirculation rate therefor.

BACKGROUND OF THE INVENTION

In blood purification treatment, e.g., dialysis treatment, a blood circuit formed from flexible tubes is generally used to circulate the patient's blood extracorporeally. The blood circuit is formed primarily from an arterial blood circuit to which an arterial needle is attached to an end to collect blood from the patient and a venous blood circuit to which a venous needle is attached to an end to reintroduce blood to the patient. A dialyzer is interposed between the arterial blood circuit and the venous blood circuit to purify the extracorporeally circulated blood.

This dialyzer contains a plurality of hollow fibers. Blood flows through these hollow fibers while dialysate flows outside (between the outer perimeter surfaces of the hollow fibers and the inner perimeter surface of the case). The hollow fibers are formed with a plurality of micropores on its walls, and the waste products and the like of the blood flowing through the hollow fibers pass through a blood purification membrane and are discharged into the dialysate. The purified blood from which the waste products have been discharged is then reintroduced to the body of the patient. An ultrafiltration pump is provided to remove water from the patient's blood in the dialyzer so that ultrafiltration can be performed during dialysis treatment.

When, for example, extracorporeal circulation is performed by applying the arterial needle and the venous needle to a patient's shunt (an access vessel provided by a surgical operation that connects an artery and vein) and its vicinity, blood recirculation can take place, where the blood from the venous needle that has been purified and reintroduced to the patient's body can be reintroduced into the arterial needle without having passed through the patient's organs and the like. When this type of blood recirculation takes place, purified blood is further circulated extracorporeally, reducing the flow of extracorporeal circulation of blood that needs to be purified, leading to lower blood purification efficiency. Also, if blood recirculation takes place, a device for detecting the concentration of the extracorporeally circulating blood such as a blood volume measuring device (hematocrit sensor) will not provide values that reflect the blood concentration for the patient's whole body, preventing reliable data from being obtained.

Accordingly, as described in JP2001-502590 (a Published Japanese Translation of a PCT Application), a conventional hemodialysis apparatus has been proposed wherein an indicator in the form of a concentration agglomeration is applied to the extracorporeally circulating blood suddenly and in a short period of time. This indicator (concentration agglomeration) is detected, and the area ratio of the detection signal indicating the change in blood concentration of the obtained indicator is used to calculate a recirculation rate. With the hemodialysis apparatus described in this document, a recirculation rate can be measured in a short period of time.

SUMMARY OF THE INVENTION

However, the conventional blood purification apparatus described above had the following problems.

When there is a stenosis or the like at the patient's access vessel (shunt) and the blood flow through the access vessel is less than the extracorporeally circulating blood flow, it is believed that blood recirculation takes place in order to satisfy the extracorporeally circulating blood flow and to compensate for the insufficient blood flow coming through the access vessel. More specifically, when a predetermined extracorporeal circulation flow is to be provided by driving a blood pump, insufficient blood flow at the access vessel can lead to blood flowing from the venous needle to the arterial needle, resulting in blood recirculation.

While the conventional blood purification apparatus can detect blood recirculation, there was no suggestion of what measures should be taken after blood recirculation is detected to provide good blood purification. More specifically, with the current state of technology, if considerable blood recirculation is found, the medical staff, e.g., a physician, responds by changing the position of the needle or the like. However, if blood recirculation takes place because the blood flowing through the access vessel is less than the extracorporeal blood flow as described above, changing the needle position will not prevent blood recirculation.

The object of the present invention is to overcome these problems and to provide a blood purification apparatus and a recirculation calculation method thereof that indicates a measure to be taken to reduce blood recirculation and improve blood purification even if the blood recirculation takes place because the blood flow through the access vessel of the patient is less than the extracorporeal circulation.

According to the first aspect of the present invention, a blood purification apparatus includes a blood circuit formed from an arterial blood circuit and a venous blood circuit to extracorporeally circulate blood retrieved from an access vessel of a patient, a blood pump provided in the arterial blood circuit, means for purifying blood connected between the arterial blood circuit and the venous blood circuit and purifying blood flowing through the blood circuit, means for applying an indicator applying a predetermined indicator to the blood flowing extracorporeally through the blood circuit, means for detecting the indicator applied by indicator applying means, and arithmetic means capable of calculating, based on the indicator detected by detecting means, a recirculation rate, which is a proportion relative to an extracorporeally circulating blood flow of recirculated blood reintroduced to the patient from the venous blood circuit and directed again to the arterial blood circuit. The blood purification apparatus also includes means for calculating an ideal extracorporeally circulating blood flow that results in the recirculation rate being no more than a predetermined value when the recirculation rate calculated by the arithmetic means is greater than the predetermined value.

According to the second aspect of the present invention, in the blood purification apparatus according to the first aspect, the blood pump is controlled in tandem to provide the ideal extracorporeally circulating blood flow calculated by the calculating means.

According to the third aspect of the present invention, in the blood purification apparatus according to the first or second aspect, the ideal extracorporeally circulating blood flow results in a recirculation rate of approximately 0.

According to the forth aspect of the present invention, in the blood purification apparatus according to any one of the first through third aspect, the calculating means uses a recirculation rate ($\alpha$) calculated by the arithmetic means to determine a shunt flow (Qf), which is a blood flow through the access vessel of the patient, and calculates the ideal extracorporeally circulating blood flow based on the shunt flow (Qf).

According to the fifth aspect of the present invention, in the blood purification apparatus according to the fourth aspect, the calculating means determines the shunt flow (Qf) using a formula shunt flow (Qf)=(1−recirculation rate ($\alpha$))×(extracorporeally circulating blood flow (Qb)).

According to the sixth aspect of the present invention, a method for calculating a recirculation rate for a blood purification apparatus is provided. In the method, blood retrieved from an access vessel is extracorporeally circulated through a blood circuit formed from an arterial blood circuit and a venous blood circuit. The blood is purified by blood purifying means connected between the arterial blood circuit and the venous blood circuit. A predetermined indicator is applied in the blood circuit to the extracorporeally circulating blood. The indicator is detected, thereby allowing calculation of a proportion of the recirculation of blood reintroduced to the patient from the venous blood circuit and reintroduced to the arterial blood circuit relative to the extracorporeally circulating blood flow. An ideal extracorporeally circulating blood flow is calculated to make the recirculation rate no more than a predetermined value.

According to the seventh aspect of the present invention, in the method according to the sixth aspect, the ideal extracorporeally circulating blood flow wherein the recirculation rate is made approximately 0.

According to the eighth aspect of the present invention, in the method according to the sixth or seventh aspect, a calculated recirculation rate ($\alpha$) is used to determine a shunt flow (Qf), which is a blood flow through an access vessel of a patient, and the ideal extracorporeally circulating blood flow is calculated based on the shunt flow (Qf).

According to the ninth aspect of the present invention, in the method according to the eighth aspect, the shunt flow (Qf) is determined using a formula shunt flow (Qf)=(1−recirculation rate ($\alpha$))×(extracorporeally circulating blood flow (Qb)).

With the present invention, an ideal extracorporeally circulating blood flow is calculated to provide a recirculation rate that is no more than a predetermined value. Even if the blood flowing through the access vessel of the patient is lower than the extracorporeally circulation blood flow, resulting in blood recirculation, a measure to be taken to provide effective blood purification with reduced blood recirculation can be indicated. In particular, with the invention according to the second aspect, the blood pump is controlled in tandem to achieve the ideal extracorporeally circulating blood flow calculated by calculating means. This reduces the recirculation rate to no more than the predetermined value during blood purification treatment. With the invention according to the third and seventh aspect, an ideal extracorporeally circulating blood flow is calculated to make the recirculation rate approximately 0. Thus, no blood recirculation takes place, and blood purification treatment can be performed more efficiently.

DETAILED DESCRIPTION OF THE INVENTION

An embodiment of the present invention will be described in detail, with references to the figures.

Figure 1:
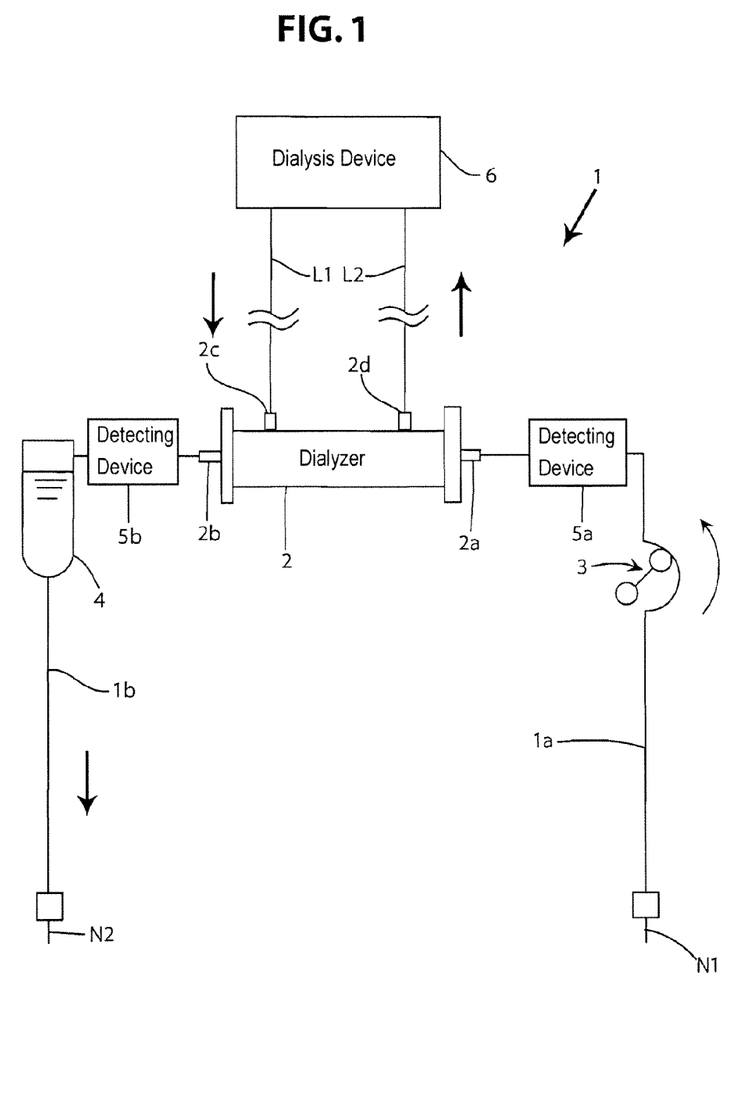
FIG. 1 is a schematic diagram of a blood purification apparatus according to an embodiment of the present invention.

A blood purification apparatus according to this embodiment purifies the blood of a patient while circulating the blood extracorporeally and is implemented for a hemodialysis apparatus used in dialysis treatment. As shown in FIG. 1, the hemodialysis apparatus is provided with a blood circuit 1 to which is connected a dialyzer 2 serving as a blood purification device, and a dialysis device 6 supplying dialysate to the dialyzer 2 while removing water. As shown in the figure, the blood circuit 1 is provided with an arterial blood circuit 1a and a venous blood circuit 1b, and made of flexible tubes. The dialyzer 2 is connected between the arterial blood circuit 1a and the venous blood circuit 1b.

The arterial blood circuit 1a is connected to an arterial needle N1 at an end of the circuit 1a, and provided with a peristaltic blood pump 3 and a first detecting device 5a. The venous blood circuit 1b is connected to a venous needle N2 at an end of the circuit 1b, and provided with a second detecting device 5b and a drip chamber 4 that removes bubbles.

With the arterial needle N1 and the venous needle N2 inserted into the shunt (an access vessel provided by a surgical operation that connects an artery and vein), the blood pump 3 is operated. The blood of the patient is collected from the access vessel and passes through the arterial blood circuit 1a to reach the dialyzer 2, with the dialyzer 2 purifying the blood. Bubbles are removed at the drip chamber 4 and the blood passes through the venous blood circuit 1b to be returned into the patient's body. Thus, the blood is dialyzed by the dialyzer 2 during extracorporeal circulation through the blood circuit 1.

The dialyzer 2 is formed with a blood inlet port 2a, a blood outlet port 2b, a dialysate inlet port 2c and a dialysate outlet port 2d, provided in the case of the dialyzer 2. The other end of the arterial blood circuit 1a is connected to the blood inlet port 2a while the other end of the venous blood circuit 1b is connected to the blood outlet port 2b. The dialysate inlet port 2c and the dialysate outlet port 2d are connected to the dialysate inlet line L1 and the dialysate outlet line L2, which are extended from the dialysis device 6, respectively.

The dialyzer 2 includes a plurality of hollow fibers. The blood flows through the inside of the hollow fibers, and the dialysate flows between outside surfaces of the hollow fibers and an inside surface of the case. The hollow fibers are provided with a plurality of micropores on the inside and outside surfaces of the hollow fibers. This forms permeable membranes which allow waste products in the blood to permeate into the dialysate.

Figure 2:
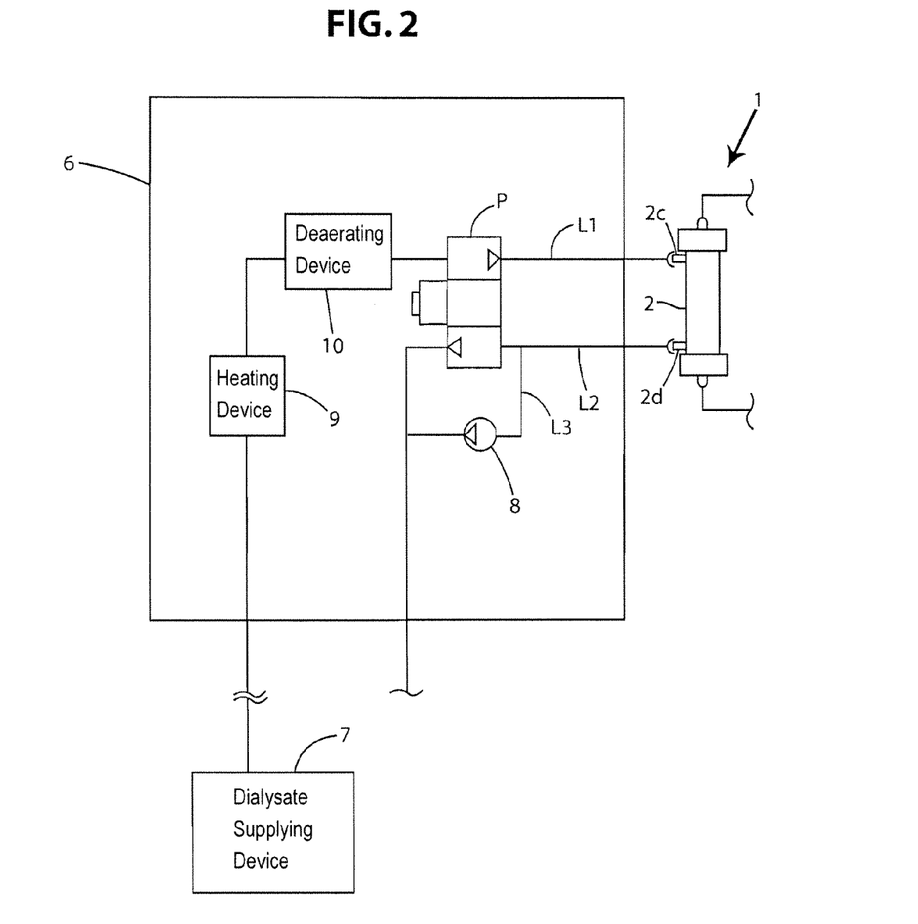
FIG. 2 is a schematic diagram of a dialysis device in the blood purification apparatus.

As shown in FIG. 2, the dialysis device 6 includes a duplex pump P, a bypass line L3, and an ultrafiltration pump 8. The duplex pump P is connected to both the dialysate inlet line L1 and the dialysate outlet line L2, bridging those two lines L1 and L2. The bypass line L3 is connected to the dialysate inlet line L2 bypassing the duplex pump P, and is also connected to the ultrafiltration pump 8 (indicator application device). The dialysate inlet line L1 is connected at one end thereof to the dialyzer 2 (the dialysate inlet port 2c), and at another end thereof to a dialysate supplying device 7 that prepares the dialysate of a predetermined concentration.

The dialysate outlet line L2 is connected at one end thereof to the dialyzer 2 (dialysate outlet port 2d), and at another end thereof to a fluid disposal device (not shown). The dialysate supplied from the dialysate supplying device 7 flows through the dialysate inlet line L1 into the dialyzer 2, then, flows through the dialysate outlet line L2 and the bypass line L3 into the fluid disposal device. The figure also shows a heating device 9 and a deaerating device 10 connected to the dialysate inlet line L1.

The ultrafiltration pump 8 is used to remove water from the blood of the patient flowing through the dialyzer 2. When the ultrafiltration pump 8 is activated, a volume of the dialysate flowing out from the dialysate outlet line L2 becomes greater than a volume of the dialysate flowing in through the dialysate inlet line L1 because the duplex pump P is a metering pump. Accordingly, water is removed from the blood by the difference between the volumes flowing out and flowing in. Devices other than the ultrafiltration pump 8 (e.g., a balancing chamber) may be used to remove water from the blood.

The ultrafiltration pump 8, which serves as the indicator application device in this embodiment, performs the water removal needed for dialysis treatment while also allowing water removal to be performed suddenly and in a short period of time. More specifically, the water removal taking place at a fixed rate during dialysis treatment can be paused (although extracorporeal circulation continues), and once the measured hematocrit value becomes stable the ultrafiltration pump 8 can be activated suddenly and over a short period of time to remove water, thus applying a characteristic peak to the change in blood concentration (hematocrit value). The "sudden and over a short period of time" referred to in the present invention indicates a magnitude and duration that makes it possible for the pulse to be confirmed after the circuit has been traversed. "Characteristic" means that the pulse can be distinguished from variation patterns resulting from other factors such as variations in the pump or movement of the patient's body.

Figure 3:
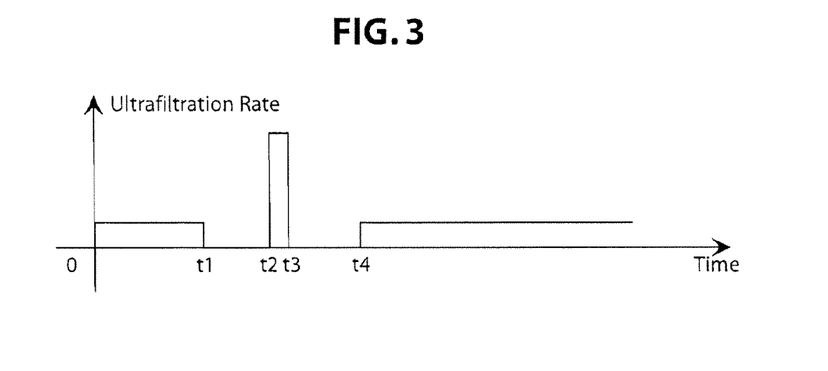
FIG. 3 is a graph showing how an ultrafiltration pump in the blood purification apparatus is controlled and illustrating how ultrafiltration is performed suddenly and in a short period of time.
Figure 4:
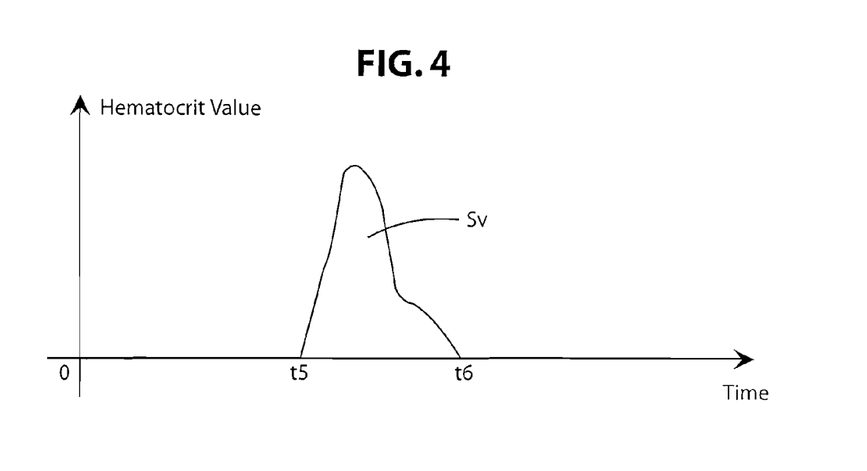
FIG. 4 is a graph showing the change in a hematocrit value detected by a second detecting device in the blood purification apparatus.

As shown in FIG. 3, more specifically, the water removal at a fixed rate (normal water removal) is stopped at time t1. When the measured hematocrit value subsequently becomes stable at time t2, the ultrafiltration pump 8 is operated at a higher rate than normal until time t3. The interval from time t2 to time t3 is very short. This makes it possible to perform water removal suddenly and in a short time compared to normal water removal. This provides a characteristic peak, e.g., as shown in FIG. 4, in the hematocrit value.

The first detecting device 5a and the second detecting device 5b are provided in the arterial blood circuit 1a and the venous blood circuit 1b respectively and detect the concentration of the blood (specifically, the hematocrit value) flowing through their respective circuits. This makes it possible to detect the indicator applied by the ultrafiltration pump 8 (the characteristic peak applied to the blood concentration (hematocrit value) by the sudden and short-duration water removal). The first detecting device 5a and the second detecting device 5b are formed from hematocrit sensors. These hematocrit sensors can, for example, contain a light-emitting element such as an LED and a light-receiving element such as a photodiode. The hematocrit value indicating the concentration of the blood of the patient is detected by shining the light from the light-emitting element to the blood and using the light-receiving element to receive the light transmitted through or reflected from the blood.

More specifically, the hematocrit value indicating the concentration of the blood is determined based on the electrical signal output from the light-receiving element. The components of the blood such as red blood cells and plasma have unique light absorption characteristics. The hematocrit value can be determined by using these characteristics to photoelectrically provide the quantification of the red blood cells needed to measure the hematocrit value. More specifically, near infrared light from the light-emitting element enters the blood and is absorbed/scattered and enters the light-receiving element. Based on the strength of the received light, the absorption and scattering rates of the light are analyzed and the hematocrit value is calculated.

The first detecting device 5a formed as described above is provided in the arterial blood circuit 1a, and the hematocrit value is detected for the blood retrieved from the patient by way of the arterial needle N1 during dialysis treatment. The second detecting device 5b is provided in the venous blood circuit 1b, and the hematocrit value of the blood purified by the dialyzer 2 and reintroduced to the patient is measured. More specifically, the characteristic peak applied by the ultrafiltration pump 8 is detected first by the second detecting device 5b (see FIG. 4), and then, if the blood reaches the arterial blood circuit 1a again and there is recirculation, the first detecting device 5a detects the characteristic peak that remains in the recirculated blood (see FIG. 5).

Thus, it is possible to determine whether or not the ultrafiltration pump 8 applied a characteristic peak using the second detecting device 5b, and the first detecting device 5a can detect whether or not there is recirculated blood. More specifically, since it is possible to determine whether or not the ultrafiltration pump 8 applied a characteristic peak, blood recirculation can be detected reliably and precisely compared to an apparatus in which a detecting device is provided only in the arterial blood circuit.

Figure 6:
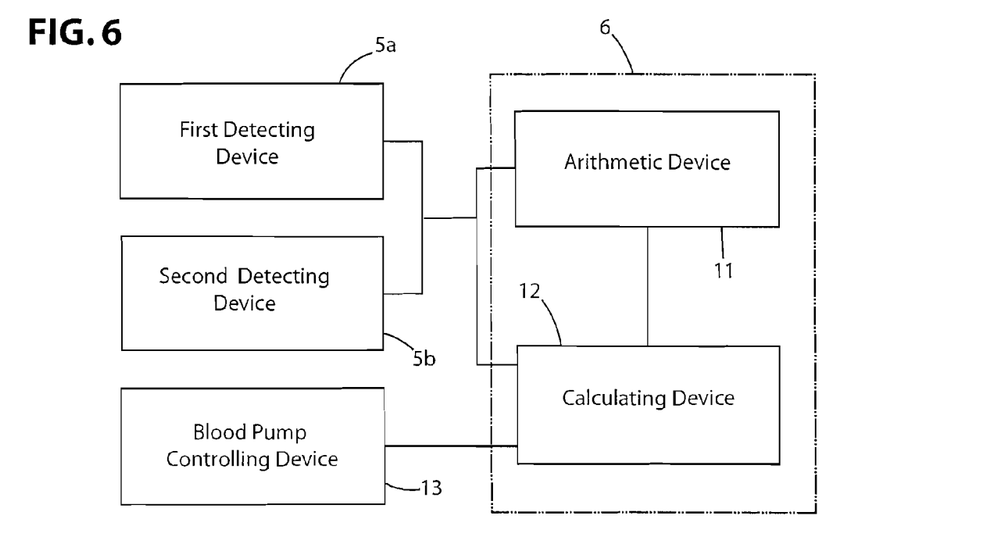
FIG. 6 is a block diagram showing the connections between the first detecting device, the second detecting device, the arithmetic device, the blood pump controlling device, and the calculating device in the blood purification apparatus.

Furthermore, as shown in FIG. 6, the first detecting device 5a and the second detecting device 5b are electrically connected to an arithmetic device 11 provided in the dialysis device 6. The arithmetic device 11, formed from a microprocessor or the like, can compare the hematocrit value (characteristic peak) detected by the first detecting device 5a and the second detecting device 5b and calculate the proportion of recirculated blood in the blood flowing through the arterial blood circuit 1a. The arithmetic device 11 can calculate, based on the characteristic peak (indicator) detected by the first detecting device 5a and the second detecting device 5b, a recirculation rate that is a proportion of a flow of recirculated blood, which is reintroduced to the patient from the venous blood circuit 1b and guided back to the arterial blood circuit 1a, relative to a flow of extracorporeally circulating blood.

More specifically, if there is blood recirculation, the ultrafiltration pump 8 applies a characteristic peak (indicator). The time for the blood to reach the second detecting device 5b (time t5 in FIG. 4) and the time for the blood to be recirculated and reach the first detecting device 5a (t7 in FIG. 5) are predicted. The arithmetic device 11 compares the hematocrit value detected by the second detecting device 5b when time t5 has elapsed and the hematocrit value detected by the first detecting device 5a when time t7 has elapsed.

By predicting time t5 for the blood to reach the second detecting device 5b and the time t7 for the blood to recirculate and reach the first detecting device 5a, it is possible to distinguish between cardiopulmonary recirculation (a phenomenon that a portion of purified blood passes through only the heart or lungs and is led to the extracorporeal circulation without passing through other tissue, organs, or the like) and the recirculation to be measured. Also, instead of this method, it would also be possible to have the arithmetic device 11 recognize when the hematocrit values detected by the first detecting device 5a and the second detecting device 5b exceed a predetermined value and to compare these hematocrit values that have exceeded this value.

Figure 5:
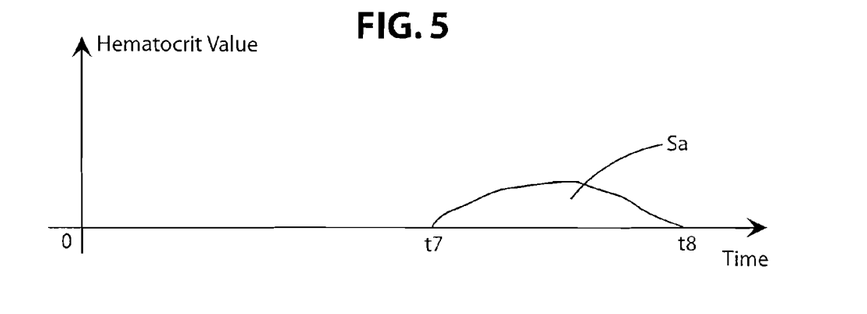
FIG. 5 is a graph showing the change in a hematocrit value detected by a first detecting device in the blood purification apparatus when there is recirculation.

Then, as shown in FIG. 4 and FIG. 5, the change in the hematocrit value in the first detecting device 5a and the second detecting device 5b is determined based on a time-hematocrit value graph, and the area of the time interval to be compared (the section with the change) is calculated mathematically, e.g., by integrating. For example, if the area of the section with the change based on the second detecting device 5b (the section from t5 to t6 in FIG. 4) is Sv and the area with the section with the change based on the first detecting device 5a (the section from t7 to t8 in FIG. 5) is Sa, the proportion of recirculated blood (recirculation rate) Rrec can be determined using the following formula.

$$Rrec\ (\%) = Sa/Sv \times 100 \quad \text{(Formula 1)}$$

The time for the section with the change based on the first detecting device 5a (the interval from t7 to t8) is set longer than time for the section with the change based on the second detecting device 5b (the interval from t5 to t6) in order to take into account the dispersion that takes place when blood to which the characteristic peak has been applied flows from the second detecting device 5b to the first detecting device 5a. The obtained proportion of recirculated blood is displayed on a displaying device (not shown in the figure) provided on the dialysis device 6 so that it is available for visual confirmation by the medical staff, e.g., a physician. If there is no blood recirculation, Sa is 0 and the value displayed as the proportion of the recirculated blood will be 0 (%). Thus, in addition to whether or not there is blood recirculation, the medical staff can be aware of what the proportion is so that it can be used as reference for the subsequent measure taken (reinserting a needle to prevent blood recirculation or reforming the shunt).

The embodiment shown in FIG. 6 includes the arithmetic device 11, the first detecting device 5a, the second detecting device 5b, a blood pump controlling device 13 that controls the blood pump 3, and a calculating device 12 electrically connected to these elements. As with the arithmetic device 11, the calculating device 12 is formed from a microprocessor or the like. If the recirculation rate calculated by the arithmetic device 11 is greater than a predetermined value (e.g., 10%), an ideal extracorporeal blood flow that would make the recirculation rate no more than the predetermined value set up ahead of time can be calculated.

More specifically, when the results of the operations performed by the arithmetic device 11 indicate that the current recirculate rate in the hemodialysis treatment is at least a predetermined value, the calculating device 12 uses the recirculation rate ($\alpha$) calculated by the arithmetic device 11 to determine a shunt flow (Qf), which is the blood flow through the access vessel. Based on the shunt flow (Qf), the calculating device 12 also calculates an ideal extracorporeal blood flow that would make the recirculation rate no more than a predetermined value (a value in a range where blood purification efficiency is not significantly affected and the blood concentration value detected by a hematocrit sensor or the like is not significantly affected).

If the shunt flow (Qf) is lower than the extracorporeally circulating blood flow (Qb) due to stenosis at the access vessel (shunt) or the like, blood recirculation would be expected to take place to satisfy the extracorporeal circulating blood flow and to compensate for the insufficient blood flow coming through the access vessel. Thus, the following formula would be established, where Qr is the blood recirculation flow, and Qb is the extracorporeally circulating blood flow.

$$Qb = Qf + Qr \quad \text{(Formula 2)}$$

The recirculation rate ($\alpha$) is the proportion of the recirculation blood flow (Qr) relative to the extracorporeally circulating blood flow (Qb), so $\alpha = Qr/Qb$. When this relationship is substituted into Formula 1 above, the following relationship is established.

$$Qb = Qf + \alpha \cdot Qb$$

$$Qf = (1 - \alpha) Qb \quad \text{(Formula 3)}$$

The extracorporeally circulating blood flow (Qb) is determined from the level of activity of the blood pump 3 (i.e., the control provided by the blood pump controlling device 13). The shunt flow (Qf) for the extracorporeally circulating blood flow (Qb) can be determined by substituting the extracorporeally circulating blood flow (Qb) and the recirculation rate ($\alpha$) determined from Formula 1 into Formula 3 above.

If the shunt flow (Qf) is determined in this manner, it is possible to determine an ideal extracorporeally circulating blood flow that will set the recirculation rate (a) to a predetermined value or less. More specifically, since the shunt flow (Qf) is always constant regardless of changes in the extracorporeally circulating blood flow, it can be seen from the relationship in Formula 3 that the recirculation rate ($\alpha$) can be set to 0 (i.e., no blood recirculation) by using an extracorporeally circulating blood flow (ideal extracorporeally circulating blood flow) that is the same as the shunt flow (Qf).

In particular, almost all of the shunt flow (Qf) can be set to circulate extracorporeally by setting the predetermined value set up ahead of time to approximately 0 and calculating the ideal extracorporeally circulating blood flow so that the recirculation rate ($\alpha$) is approximately 0. This prevents blood recirculation and makes it possible to provide more efficient blood purification treatment.

Furthermore, in this embodiment, the calculating device 12 sends a control signal to the blood pump controlling device 13 so that the blood pump 3 is operated to produce the ideal extracorporeally circulating blood flow determined by the calculating device 12 as described above. As a result of the calculations performed by the arithmetic device 11, if the current recirculation rate during hemodialysis treatment is at least a predetermined value, the calculating device 12 calculates an ideal extracorporeally circulating blood flow as described above that will result in a recirculation rate that is no more than the predetermined value (ideally, 0), and the blood pump 3 is controlled in tandem to provide this ideal extracorporeally circulating blood flow (in this case, controlled to reduce the extracorporeally circulating blood flow).

Thus, during blood purification treatment, the recirculation rate can automatically be set to be no more than a predetermined value. Also, in this embodiment, the blood pump 3 provided in the blood circuit 1 is controlled to provide an extracorporeally circulating blood flow (ideal extracorporeally circulating blood flow) that will not lead to blood recirculation. This eliminates the need to provide a separate driving device to provide the ideal extracorporeally circulating blood flow. It would also be possible to have a driving device separate from the blood pump 3 to provide an ideal extracorporeally circulating blood flow that results in a recirculation rate that is no more than the predetermined value.

With the embodiment described above, an ideal extracorporeally circulating blood flow is calculated so that the recirculation rate that is no more than a predetermined value. Thus, even if blood recirculation takes place because the blood flow through the access vessel of the patient (shunt flow (Qf)) is less than the extracorporeally circulating blood flow (Qb), a measure to provide effective blood purification with reduced blood recirculation can be indicated.

If there is surplus extracorporeal blood circulation with a shunt flow (Qf) that is greater than the extracorporeally circulating blood flow (Qb), then the blood pump 3 can be controlled to increase the extracorporeally circulating blood flow. For example, when treatment is performed using the calculated ideal extracorporeally circulating blood flow, one possible outcome, in addition to the detected recirculation rate (α) being "0" or the shunt flow (Qf) being the same as the actual extracorporeally circulating blood flow, is for the shunt flow (Qf) to be greater than the extracorporeally circulating blood flow, leading to surplus extracorporeal circulation. In this case, the blood pump can be controlled to increase the extracorporeally circulating blood flow in stages and to detect when the shunt flow (Qf) is the same as the actual extracorporeally circulating blood flow (i.e., when all the blood flowing through the shunt is extracorporeally circulated).

An embodiment of the present invention was described above, but the present invention is not restricted to this. For example, it would be possible to display the ideal extracorporeally circulating blood flow calculated by the calculating device 12 on a screen or the like and to have the blood pump 3 controlled manually by medical staff, e.g., a physician, so that the circulated blood is the same as the ideal extracorporeally circulating blood flow. For the present invention, it is sufficient for there to be a calculation of the ideal extracorporeally circulating blood flow to indicate a measure to be taken to provide effective blood purification.

Also, in this embodiment, a characteristic peak is applied by having the ultrafiltration pump 8 perform a sudden and short-interval removal of water, and this is used as an indicator. However, it would also be possible to provide other means for applying an indicator. More specifically, it is sufficient to apply a predetermined indicator to the blood that is flowing extracorporeally through the blood circuit 1 so that the recirculation of blood can be detected. In addition to increasing the blood concentration as in this embodiment, it would also be possible to dilute the blood concentration suddenly and over a short interval by injecting physiological salt solution or the like. Alternatively, a sudden and short-interval temperature change can be applied.

Furthermore, in this embodiment, two detecting means 5a, 5b are used to detect the indicator applied by the indicator applying device. However, it would also be possible to detect the indicator using a single detecting device provided on the blood circuit 1. Also, the detecting device can be formed from something other than a hematocrit sensor as long as it can detect the indicator (characteristic peak) (e.g., a sensor that can detect hemoglobin concentration or a sensor that can detect the concentration of protein or the like).

Furthermore, it would be possible to sound an alarm to warn the medical staff when the proportion of recirculated blood (recirculation rate) exceeds a predetermined value. In this embodiment, the dialysis device 6 is formed as a dialysis monitoring apparatus that does not contain a dialysate supplying mechanism. However, it would also be possible to apply the present invention to a hemodialysis apparatus for individual patients that contains a dialysate supplying mechanism.

A blood purification apparatus and method for calculating a recirculation rate for the same calculates an ideal extracorporeally circulating blood flow that reduces the recirculation rate to a value no more than a predetermined value. The present invention can be used for other treatments that perform blood purification while extracorporeally circulating blood (e.g., blood filtering treatments and blood filtering dialysis treatments). Alternatively, the present invention can be used with other features added.

What is claimed is:

1. A blood purification apparatus comprising:
a blood circuit having an arterial blood circuit and a venous blood circuit to extracorporeally circulate blood retrieved from an access vessel of a patient;
a blood pump provided in the arterial blood circuit;
a blood purifying device connected between the arterial blood circuit and the venous blood circuit and configured to purify blood flowing through the blood circuit;
an ultrafiltration device configured to apply a predetermined characteristic peak indicator to the blood flowing extracorporeally through the blood circuit, wherein the predetermined characteristic peak indicator is formed only by stopping the ultrafiltration device previously set at a fixed rate, and starting and operating the ultrafiltration device at a higher rate than the fixed rate for a period of time;
a detecting device configured to detect the indicator applied by the ultrafiltration device;
an arithmetic device capable of calculating, based on the indicator detected by the detecting device, a recirculation rate; and
a calculating device configured to calculate an ideal extracorporeally circulating blood flow based on the recirculation rate, and communicate with the blood pump so that the recirculation rate is no more than a predetermined value when the recirculation rate calculated by the arithmetic device is greater than the predetermined value, wherein
the recirculation rate is a proportion of a recirculated blood flow, which is reintroduced to the patient from the venous blood circuit and directed again to the arterial blood circuit, relative to an extracorporeally circulating blood flow.

2. The blood purification apparatus according to claim 1, wherein the blood pump is controlled to provide the ideal extracorporeally circulating blood flow calculated by the calculating device.

3. The blood purification apparatus according to claim 1, wherein the ideal extracorporeally circulating blood flow results in the recirculation rate of approximately 0.

4. The blood purification apparatus according to claim 1, wherein the calculating device uses the recirculation rate (a) calculated by the arithmetic device to determine a shunt flow (Qf), which is a blood flow through the access vessel of the patient, and calculates the ideal extracorporeally circulating blood flow based on the shunt flow (Qf).

5. The blood purification apparatus according to claim 4, wherein the calculating device determines the shunt flow (Qf) using a formula below:

the shunt flow $(Qf)=(1-\text{the recirculation rate }(a))\times(\text{the extracorporeally circulating blood flow }(Qb))$.

6. The blood purification apparatus of claim 1, wherein the predetermined characteristic peak indicator comprises the removal of water.

7. The blood purification apparatus of claim 1, wherein the predetermined characteristic peak indicator comprises diluting the blood suddenly.

8. A method for calculating a recirculation rate for a blood purification apparatus, comprising:
   extracorporeally circulating blood retrieved from an access vessel through a blood circuit having an arterial blood circuit and a venous blood circuit;
   purifying the blood by a blood purifying device connected between the arterial blood circuit and the venous blood circuit;
   applying a predetermined characteristic peak indicator via an ultrafiltration device in the blood circuit to the extracorporeally circulating blood, consisting of the steps of:
      first, turning off the ultrafiltration device previously set at a fixed rate; and
      second, turning on, and operating, the ultafiltration device at a higher rate than the fixed rate for a period of time;
   detecting the indicator to calculate a recirculation rate that is a proportion of a recirculated blood flow, which is reintroduced to the patient from the venous blood circuit and directed back to the arterial blood circuit, relative to an extracorporeally circulating blood flow; and
   calculating an ideal extracorporeally circulating blood flow based on the recirculation rate to make the recirculation rate no more than a predetermined value when the recirculation rate is calculated in the detecting.

9. The method for calculating a recirculation rate for a blood purification apparatus according to claim 8, wherein, in the ideal extracorporeally circulating blood flow, the recirculation rate is made approximately 0.

10. The method for calculating a recirculation rate for a blood purification apparatus according to claim 8, wherein a calculated recirculation rate (a) is used to determine a shunt flow (Qf), which is a blood flow through an access vessel of a patient, and the ideal extracorporeally circulating blood flow is calculated based on the shunt flow (Qf).

11. The method for calculating a recirculation rate for a blood purification apparatus according to claim 10, wherein the shunt flow (Qf) is determined using a formula below:

$$\text{the shunt flow } (Qf) = (1 - \text{the recirculation rate } (a)) \times (\text{the extracorporeally circulating blood flow } (Qb)).$$

* * * * *